United States Patent [19]

Mackay

[11] Patent Number: 4,852,137
[45] Date of Patent: Jul. 25, 1989

[54] IMAGING OF LIGHT-OPAQUE SPECIMENS BY TRANSMISSION OF RADIATION THERETHROUGH

[75] Inventor: Craig D. Mackay, Cambridge, England

[73] Assignee: Astromed Limited, Cambridge, England

[21] Appl. No.: 107,255

[22] Filed: Oct. 9, 1987

[30] Foreign Application Priority Data

Oct. 11, 1986 [GB] United Kingdom ............... 8624446

[51] Int. Cl.$^4$ ............................................. G01J 1/24
[52] U.S. Cl. ........................................ 378/62; 378/98; 250/370.09; 250/370.15
[58] Field of Search ......... 250/370 G, 370.09, 370.15; 378/62, 98, 99, 19; 358/111

[56] References Cited

U.S. PATENT DOCUMENTS 4,298,800 11/1987 Goldman ........................... 378/19
4,553,206 11/1985 Smutek et al. ..................... 364/300

OTHER PUBLICATIONS

Derenzo, "Gamma-Ray Spectroscopy using Small Coded Bismuth Germanate Scintillators and Silicon Photodiodes", *Nuclear Instruments and Method in Physics Research*, 219 (1984) pp. 117-122.

*Primary Examiner*—Carolyn E. Fields
*Assistant Examiner*—David P. Porta
*Attorney, Agent, or Firm*—Lee & Smith

[57] ABSTRACT

A method of and apparatus for imaging light opaque specimens wherein a secondary source (16) is stimulated by radiation (x-rays or high energy electrons or neutrons) transmitted through the specimen (12) and visible light emitted by the secondary source (without amplification) is detected by a cooled slow scan CCD (26, 28) coupled to the secondary source by a lens (20) and shutter (22).

8 Claims, 1 Drawing Sheet

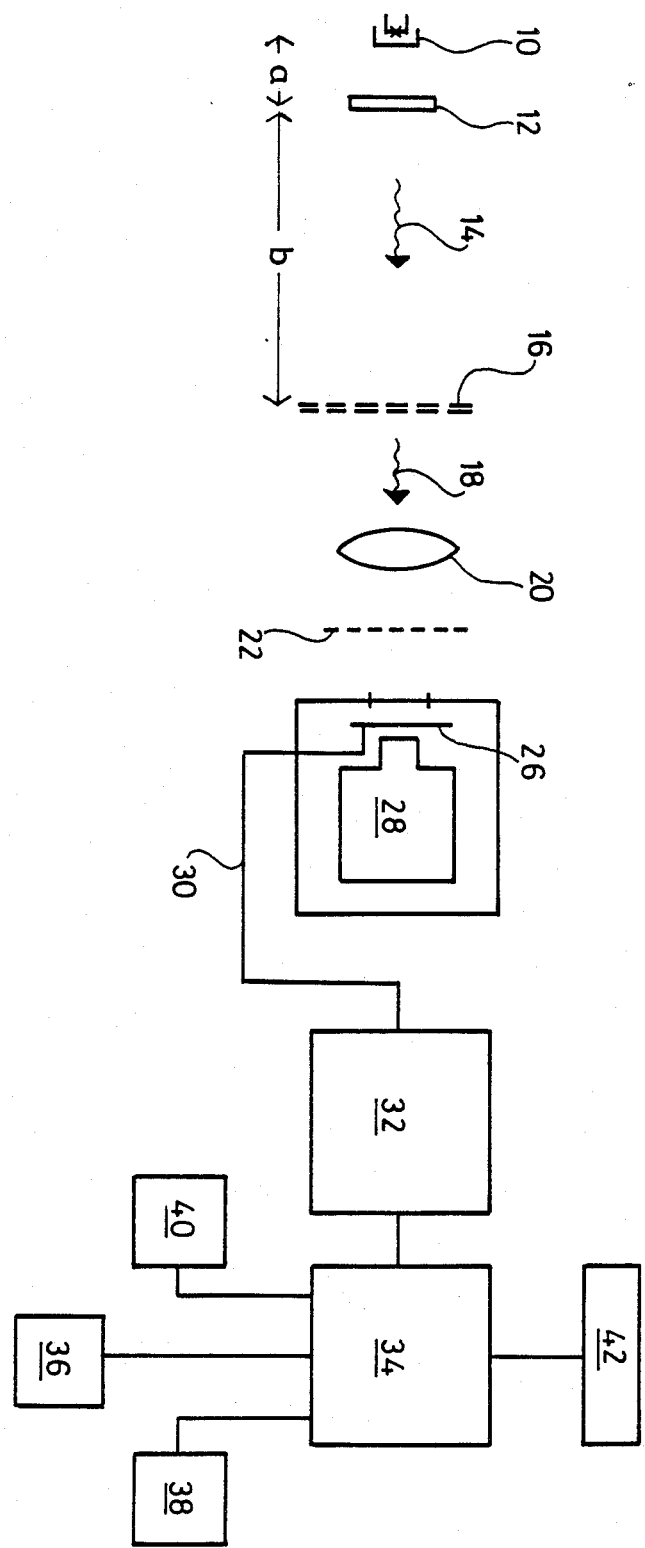

ies of 64 to 256 grey levels, restricting the
IMAGING OF LIGHT-OPAQUE SPECIMENS BY TRANSMISSION OF RADIATION THERETHROUGH

FIELD OF THE INVENTION

This invention relates to the imaging of a light-opaque specimen by the transmission of radiation therethrough. As the specimen is light-opaque, the transmitted radiation will take the form of a beam of short wavelength radiation such as X-rays or a beam of particle radiation such as electrons or neutrons, such radiation being referred to hereinafter as "penetrative radiation".

BACKGROUND TO THE INVENTION

Devices are known in which a TV camera is used to detect a visible image produced at a screen on which is imaged an energetic beam of penetrative radiation, as aforesaid, which is at least in part transmitted through a light-opaque specimen.

For example, in the transmission electron microscope (TEM), energetic electrons are accelerated and focussed on to a specimen. Those that pass through the specimen are re-imaged on to a scintillating screen which emits light when the electrons strike it. The light signal is conventionally imaged, typically by a TV camera lens coupled to the scintillating screen. In order to achieve high resolution, the electrons in the beam need to be accelerated to high energies. As a result, those that are absorbed by the specimen transfer their considerable kinetic energy to the specimen material, causing it to heat up. In many applications the heating caused by the beam current necessary to provide an adequate image on the TV camera leads to specimen damage that not only compromises the quality of the image and the results obtained but will often destroy the specimen entirely.

The situation in X-ray imaging is very similar. An X-ray source creates a point source of X-rays which pass through the specimen. X-rays for practical purposes cannot be focussed, so that all imaging is in fact a simple shadow-image of the specimen. The shadow image falls on a sheet of X-ray sensitive film or on to a phosphor screen to create a visible image which is again detected by a TV camera suitably coupled to the image. As with the electron beam case, X-ray beam damage imposes an important limitation on the kind of specimens which may be inspected with X-rays.

U.S. Pat. No. 4,503,460 discloses an X-ray diagnostic arrangement in which X-rays passing through a specimen are received by an X-ray image intensifier. By application of a high voltage the image intensifier produces a light image on a fluorescent output screen which is amplified and intensified compared with the strength of the input image. The intensifier output is optically coupled, by means of a plurality of lenses, to semiconductor image sensors such as CCD image converters, which may be cooled e.g. by Peltier elements. The outputs of the image sensors are converted into video signals, which are read and displayed at TV frame rates, i.e. in real time. The use of an image intensifier increases signal strength but also has the effect of adding noise to the signal, so compromising the quality of the final image. Further, image intensifiers need voltages of many kilovolts to operate, are prone to damage from signal overload and have poor geometric fidelity, giving up to 30% distortion at the edge of their field of view. They also have very poor dynamic range.

It is an aim of the present invention to provide a method and apparatus for imaging light opaque specimens by transmission of penetrative radiation therethrough capable of giving better results than have been possible hitherto.

THE INVENTION

According to one aspect of the present invention there is provided a method of imaging light-opaque specimens by transmission of penetrative radiation therethrough, according to which the visible light emitted at a secondary source stimulated by radiation transmitted through the specimen is imaged on to a cooled two-dimensional charge coupled device (CCD), wherein the secondary source provides no signal amplification and wherein the CCD is operated in slow scan mode.

The CCD is preferably cooled to $-40°$ C. or below, typically being operated at between $-80°$ C. and $-130°$ C., and in extreme cases being operated at temperatures down to about $-170°$ C.

In the cases of specimen imaging both with electrons and X-rays, the use of a cooled slow-scan CCD gives a dramatic improvement in the quality of the images achieved, when compared with those obtained with existing TEM and X-ray imaging systems. The cooled CCD shows excellent low light level sensitivity as well as excellent dynamic range (in excess of 100,000:1). Its principal advantages are:

1. The sensitivity of the CCD (DQE (detective quantum efficiency) in excess of 50 percent peak for P8600 devices from EEV Ltd.) allows acceptable images to be obtained with the lowest possible radiation beam energy integrated over the exposure time.

2. The long integration times possible with a cooled CCD (up to several hours) permit the lowest possible radiation beam flux, allowing the specimen to cool or otherwise recover during the exposure.

3. In many instances, and especially with X-rays, materials can be only slightly absorbing leading to a very low contrast image. Most TV cameras have dynamic ranges of 64 to 256 grey levels, restricting the ability of the system to cope with the lowest contrast features in an image, irrespective of the actual signal level. The cooled slow-scan CCD system with its 65,536 grey levels permits much lower contrast features to be measured accurately. This can be important in X-ray examination of soft tissues, for example, enabling high quality imaging with minimum dosage.

4. With more opaque samples, problems arise when the specimen only partly fills the imaged area. The unattenuated beam can produce an output image brightness great enough to stop conventional cameras being able to image the specimen of interest because of their limited dynamic range and hence poor saturation characteristics. The cooled slow-scan CCD system is able to cope with very high signals per pixel (greater than 500,000 photons detected per pixel for P8600 CCDs), without compromising the low-level imaging performance of the device.

5. In X-ray microscopy the resolution limit is set by the X-ray source spot size since X-rays cannot generally be focussed on to a small spot. Many features in materials that are of importance, such as hairline fractures, inclusions of fibres or air or gas bubbles, are only a few or a few tens of microns in diamater. Recent X-ray sources can give an X-ray source spot size as small as one micron (such as the system presently marketed by Technosyn Ltd., Coldhams Lane, Cambridge). However, the X-ray intensity is extremely low because the electron current which strikes the copper target to generate the X-rays must not be so high within the one micron spot size as to risk overheating the target. Conventional TV cameras are unable to work at a distance from the sample adequate to give the resolution justified by the one micron X-ray source spot size. An X-ray source at a sample distance of 1 cm will produce an image 50 cm from the sample with a scale of 50 times magnification, i.e. the 25 micron pixel of the TV camera will correspond to 0.5 microns in the sample, roughly the optimal imaging arrangement for maximum resolution. However, the cooled slow-scan CCD system enables precision X-ray microscopy work to be carried out with small spot size X-ray sources.

6. The CCD is lens coupled to the visible image. This enables the scintillating or like screen to be inside a vacuum chamber if necessary. It also enables variable magnification and field sizes by the provision of interchangeable or zoom lenses used to perform this coupling.

7. In some instances there is interest in using very low energy radiation beams (since specimen contrast is often improved this way). However, the signals generated are often too weak to be usable with a conventional TV camera, yet are entirely adequate when used with a cooled slow-scan CCD camera.

8. The use of a two-dimensional detector of wide dynamic range is also important for the field of X-ray tomography. By imaging a specimen twice with X-rays and a camera with the specimen rotated slightly between exposures, a stereo pair can be obtained. Such a stereo pair permits the operator to see a three-dimensional image of the specimen provided the image quality is good enough. This is because the differences between the images are small and only detector systems with excellent geometric fidelity and high dynamic range are capable of achieving this quality of imaging.

9. Use of a cooled slow scan CCD in conjunction with a secondary source which produces visible light without amplification of the incident penetrative radiation provides improved results as compared with those obtained with the arrangement described in U.S. Pat. No. 4,503,460. The prior art arrangement uses an X-ray image intensifier to increase signal strength, but this also has the effect of adding noise to the signal and so compromising the quality of the final image. In contrast, no such signal amplification is obtained with the secondary source of the present arrangement, so addition of undesirable noise at this stage is avoided: instead, image quality is improved by using a slow scan CCD, sufficiently cooled to reduce dark current. Only modest cooling (probably down to $-30°$ C. at most) is used in the prior art arrangement as dark current is of less importance for a CCD operated at TV frame rates, involving exposure times of about 40 milliseconds. Dark current increases linearly with exposure times and so is of greater significance in practicing the present invention, where read out times of minutes or hours may be used. Much greater cooling, typically between $-80°$ C. and $-130°$ C., is accordingly employed when practicing the present invention. Further, image intensifiers need voltages of many kilovolts to operate, are prone to damage from signal overload and have poor geometric fidelity, giving up to 30% distortion at the edge of their field of view. They also have very poor dynamic range. These disadvantages do not arise with the arrangement of the present invention.

According to another aspect of the invention, there is provided apparatus for imaging light-opaque specimens comprising means for generating and directing an energetic beam of penetrative radiation on to the specimen, a secondary source capable of emitting visible light without amplification as a result of stimulation by the energetic beam of radiation transmitted through the specimen, a cooled two-dimensional slow scan CCD, optical means coupling the secondary source to the CCD to image the visible light thereon, and shutter means located between the secondary source and the CCD.

DESCRIPTION OF DRAWING

The method of and apparatus for imaging in accordance with the invention are now exemplified with reference to the accompanying drawing, in which the single FIGURE shows an embodiment principally in block diagram form.

DESCRIPTION OF EMBODIMENT

The illustrated apparatus comprises a source 10 generating an energetic beam of penetrative radiation, such as an X-ray source or a source of high energy electrons or neutrons, a light-opaque specimen 12 to be imaged and through which at least part of the energetic beam 14 is transmitted, a secondary source 16 of visible light 18 such as a scintillating screen, phosphor screen or the like, a coupling lens 20, a shutter 22, and a CCD camera. The secondary source 16 absorbs the incident energetic beam, e.g. comprising X-ray photons, and emits light, thus converting penetrative radiation to light without any amplification effect.

The lens 20 couples the visible light image 18 generated at the screen 16 to the CCD camera. Exposure, from microseconds up to hours depending on circumstances, is determined by use of the shutter 22.

Magnification, in part determined by the ratio b/a, means that the system is most suitable for non-destructive small scale work, although many advantages over a conventional TV imaging system are retained even on large scale work, when the specimen requires to be positioned nearer to the screen 16 which constitutes the secondary source.

The visible light image 18 is detected by the cooled charge coupled device detector system, comprising a CCD 2000 Imaging System produced by Astromed Limited. In particular, the visible light is imaged by the coupling lens 20 on to a cooled solid-state-charge coupled device detector 26 (P8600 series CCD made by EEV Ltd.) contained inside a cold box 28 cooled with liquid nitrogen or a Sterling cycle or other mechanical or electrical cooler. Cooling down to about $-170°$ C. may be achieved, although typically temperatures of between $-80°$ C. and $-130°$ C. are used. The CCD is used in slow scan mode.

The CCD 26 is connected by electrical wiring 30 to a driver electronics unit 32 which provides the necessary drive waveforms and bias voltages for the CCD, and also processes the signal output by the CCD to minimise the overall system read-out noise. The driver electronics unit is driven and controlled by a host computer system 34 which allows operator control of the system through a VDU console 36, data archiving as represented at 38, e.g. on disk drive and on magnetic tape, and the display of the image obtained by an image display unit 40. The central computer 34 also contains software which allows analysis of the visible image of the specimen detected by the CCD. The analysis data so obtained may be output on an associated printer 42, or archived on disk or magnetic tape for storage or to allow comparison with the data obtained for other specimens.

It is to be noted that the invention is considered applicable only to static testing. The shutter is opened for such time (microseconds up to hours) as is necessary to charge the CCD for the optimum time appropriate to the overall strength and contrast of the visible image. The CCD is then read and the resulting data appropriately processed.

It is also to be understood that the CCD camera of the invention and exemplified above is operable without requiring modification of the existing X-ray sources or electron sources used in conventional TEMs and in X-ray imaging systems.

Whilst the method and apparatus of the invention has been exemplified with reference to the accompanying drawing, various modifications of the exemplary embodiment are possible within the scope of the invention.

I claim:

1. A method of imaging light-opaque specimens by transmission of penetrative radiation therethrough, comprising exposing a light-opaque specimen to penetrative radiation, permitting penetrative radiation transmitted through the specimen to impinge on a secondary source which is stimulated thereby to emit visible light without signal amplification, and imaging the emitted visible light on to a full frame two-dimensional charge coupled device (CCD) operated in slow scan mode and cooled to −40° C. or below.

2. A method according to claim 1, wherein the CCD is cooled to between −80° C. and −130° C.

3. A method according to claim 1, wherein the CCD is lens coupled to the secondary source.

4. A method according to claim 3, using an interchangeable or variable focus lens to effect the coupling.

5. A method according to claim 1, employing a scintillating screen as the secondary source.

6. A method according to claim 1, wherein the secondary source is located inside a vacuum chamber.

7. A method according to claim 1, when applied to x-ray tomography, wherein the specimen is imaged twice with said specimen slightly rotated between exposures.

8. Apparatus for imaging light-opaque specimens comprising means for generating and directing an energetic beam of penetrative radiation onto the specimen, a secondary source capable of emitting visible light without amplification as a result of stimulation by the energetic beam of radiation transmitted through the specimen, a full frame two-dimensional slow scan CCD, means for cooling said CCD to −40° C. or below, optical means coupling the secondary source to the CCD to image the visible light thereon, and shutter means located between the secondary source and the CCD.

* * * * *